United States Patent [19]

Duffett

[11] Patent Number: Plant 6,125

[45] Date of Patent: Mar. 8, 1988

[54] CHRYSANTHEMUM PLANT NAMED IRIDON

[75] Inventor: William E. Duffett, Salinas, Calif.

[73] Assignee: Yoder Brothers, Inc., Barberton, Ohio

[21] Appl. No.: 833,091

[22] Filed: Feb. 26, 1986

[51] Int. Cl.[4] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Iridon particularly characterized by its flat capitulum form; decorative capitulum type; yellow ray floret color with yellow-green inner ray florets; diameter across face of capitulum of up to 11 cm. at maturity; uniform nine week photoperiodic flowering response to short days; medium plant height when grown as a pinched disbudded pot mum; excellent plant strength under all growing conditions; and semi-spreading branching pattern.

3 Drawing Sheets

The present invention comprises a new and distinct cultivar of Chrysanthemum, botanically known as *Dentrenthema morifolium*, Ramat., previously *Chrysanthemum morifolium*, Ramat., and referred to by the cultivar name Iridon.

Iridon, identified as 81A62003, was originated from a cross made by me in a controlled breeding program in Salinas, Calif., in 1980. The female parent of Iridon was the cultivar identified as Paragon, disclosed in U.S. Plant Pat. No. 3,368. The male parent of Iridon was the cultivar identified as Pot O'Gold, disclosed in U.S. Plant Pat. No. 4,506.

Iridon was discovered and selected as one flowering plant within the progeny of the stated cross by William E. Duffett in October of 1981, in a controlled environment in Salinas, Calif.

The first act of asexual reproduction of Iridon was accomplished when vegetative cuttings were taken from the initial selection in Jan. of 1982 in a controlled environment in Salinas, Calif. by technicians working under formulations established and supervised by William E. Duffett.

Horticultural examination of controlled flowerings of successive plantings has shown that the unique combination of characteristics as herein disclosed for Iridon are firmly fixed and are retained through successive generations of asexual reproduction.

Iridon has not been observed under all possible environmental conditions. The phenotype may vary significantly with variations in environment such as temperature, light intensity and day length.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Iridon which, in combination, distinguish this Chrysanthemum as a new and distinct cultivar:

1. Flat capitulum form.
2. Decorative capitulum type.
3. Yellow ray floret color, with yellow-green inner ray florets.
4. Diameter across face of capitulum up to 11 cm. at maturity.

5. Uniform nine week photoperiodic flowering response to short days.
6. Medium plant height, requiring 0 to 7 long days after pinch prior to short days and one application of 2500 ppm B-9 SP to attain a flowered plant height of 25 to 35 cm. for year around flowerings when grown as a pinched disbudded pot mum.
7. Excellent plant strength under all growing conditions.
8. Semi-spreading branching pattern.

The accompanying photographic drawings show typical inflorescence and leaf characteristics of Iridon, with the colors being as nearly true as possible with illustrations of this type.

Sheet 1 is a color photograph of Iridon grown as a pinched disbudded pot mum.

Sheet 2 is a black and white photograph of three views of the inflorescence of Iridon.

Sheet 3 is a black and white photograph showing the upper and under sides of the leaves of Iridon at three stages of development (mature, intermediate and immature).

Of the commercial cultivars known to the inventor, the most similar in comparison to Iridon is Dark Yellow Paragon, disclosed in U.S. Plant Pat. No. 3,916. Reference is made to attached Chart A, which compares certain characteristics of Iridon to the same characteristics of Dark Yellow Paragon. Similar traits are color, capitulum type and form, branching pattern, plant height and flowering response. Iridon has a slightly smaller capitulum diameter, greater plant strength and normally develops one more break per rooted cutting after pinch than Dark Yellow Paragon.

In the following description, color references are made to The Royal Horticultural Society Colour Chart. The color values were determined on plant material grown in Salinas, Calif. on Dec. 23, 1985.

Classification:

*Botanical.*—*Dentrenthema morifolium*, Ramat., cv Iridon.

*Commercial.*—Decorative disbud pot mum.

INFLORESCENCE

A. Capitulum:

*Form.*—Flat.

*Type.*—Decorative.

*Diameter across face.*—Up to 11 cm. at maturity.

B. Corolla of ray florets:

*Color (general tonality from a distance of three meters).*—Yellow.

*Color (upper surface).*—3A, with tips of petals 3B; inner ray florets 154B to 1A.

*Color (under surface).*—4B.

*Shape.*—Oblong.

C. Corolla of disc florets:

*Color (mature).*—2A.

*Color (immature).*—144B.

D. Reproductive organs:

*Androecium.*—Present disc florets only; scant pollen.

*Gynoecium.*—Present both ray and disc florets.

PLANT

A. General appearance:

*Height.*—Medium; 25 to 35 cm. as a pinched disbudded pot mum with 0 to 7 long days after pinch prior to short days and one application of 2500 ppm B-9 SP.

*Branching pattern.*—Semi-spreading and prolific.

B. Foliage:

*Color (upper surface).*—137A.

*Color (under surface).*—147A.

*Shape.*—Deeply lobed and slightly serrated.

CHART A

COMPARISON OF IRIDON AND DARK YELLOW PARAGON

| CULTIVAR | RAY FLORET COLOR | CAPITULUM FORM & TYPE | BRANCHING PATTERN |
|---|---|---|---|
| Iridon | Yellow | Flat Decorative | Semi-Spreading |
| Dark Yellow Paragon | Yellow | Flat Decorative | Semi-Spreading |

| CULTIVAR | DIAMETER ACROSS FACE OF CAPITULUM | PLANT HEIGHT | FLOWERING RESPONSE PERIOD |
|---|---|---|---|
| Iridon | Up to 11 cm. | Medium | 9 Weeks |
| Dark Yellow Paragon | Up to 12 cm. | Medium | 9 Weeks |

COMPARISONS MADE OF PLANTS GROWN AS PINCHED DISBUDDED POT MUM IN SALINAS, CALIFORNIA

I claim:

1. A new and distinct Chrysanthemum plant named Iridon, as described and illustrated, and particularly characterized as to uniqueness by the combined characteristics of flat capitulum form; decorative capitulum type; yellow ray floret color with yellow-green inner ray florets; diameter across face of capitulum of up to 11 cm. at maturity; uniform nine week photoperiodic flowering response to short days; medium plant height when grown as a pinched disbudded pot mum; excellent plant strength under all growing conditions; and semi-spreading branching pattern.

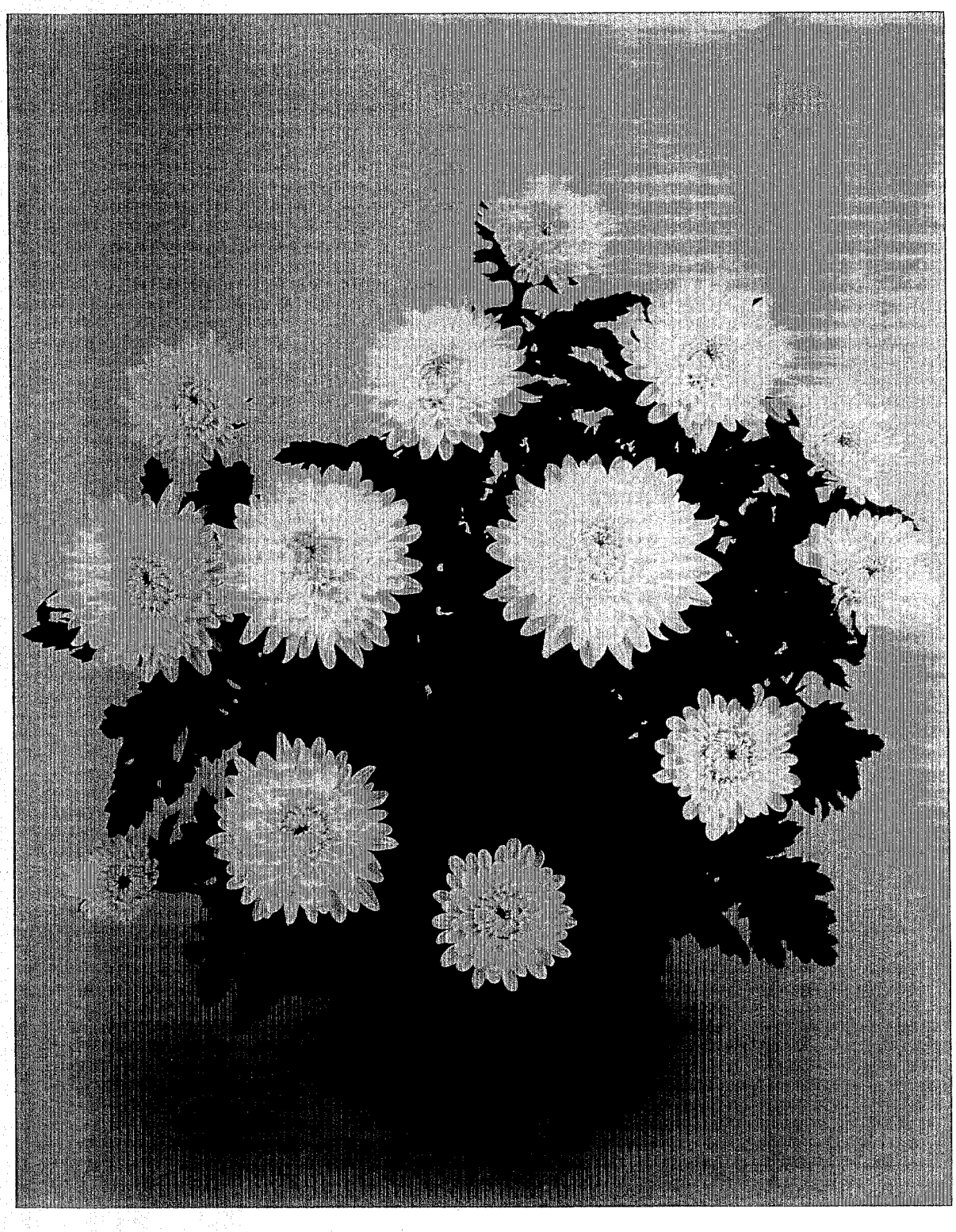

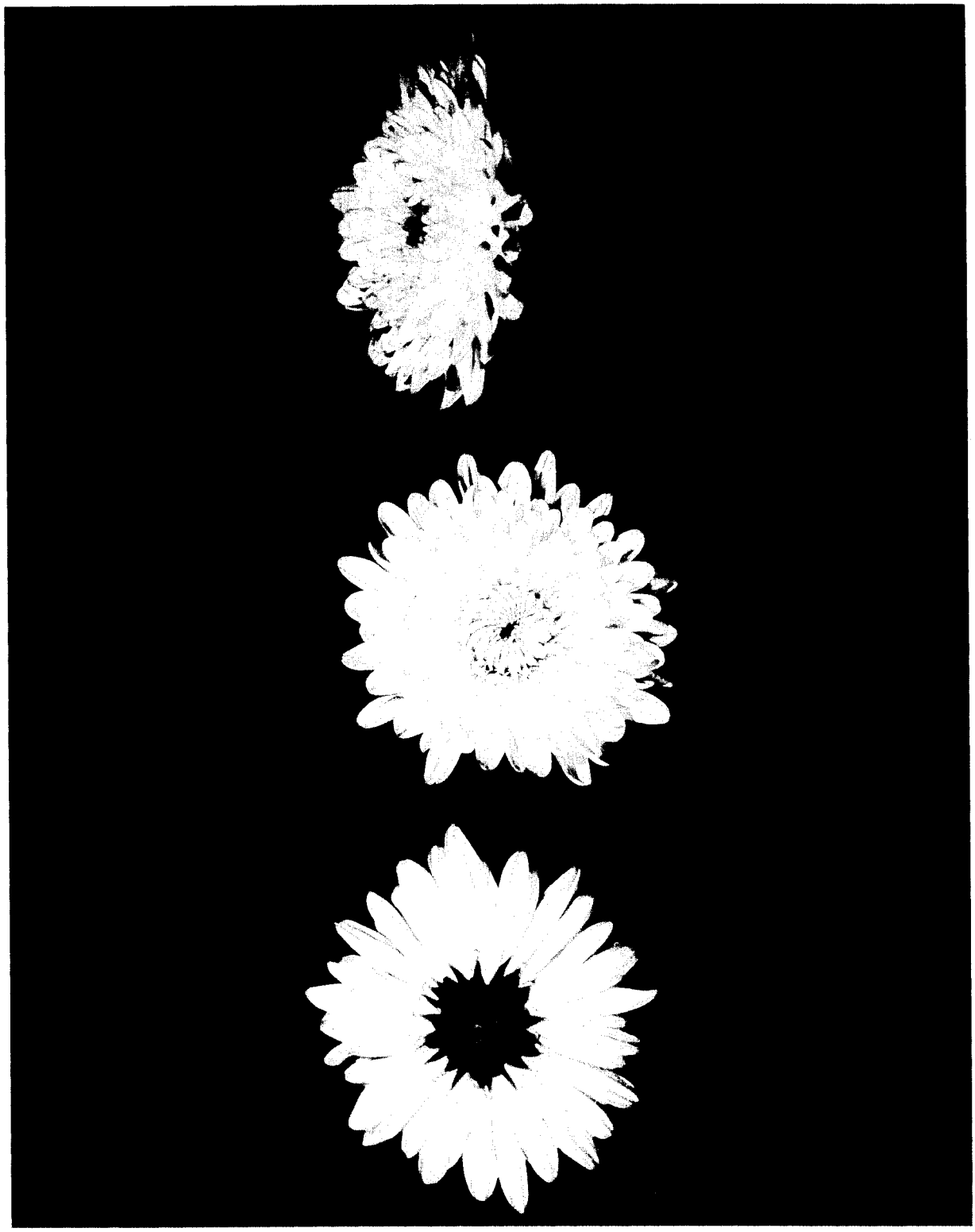

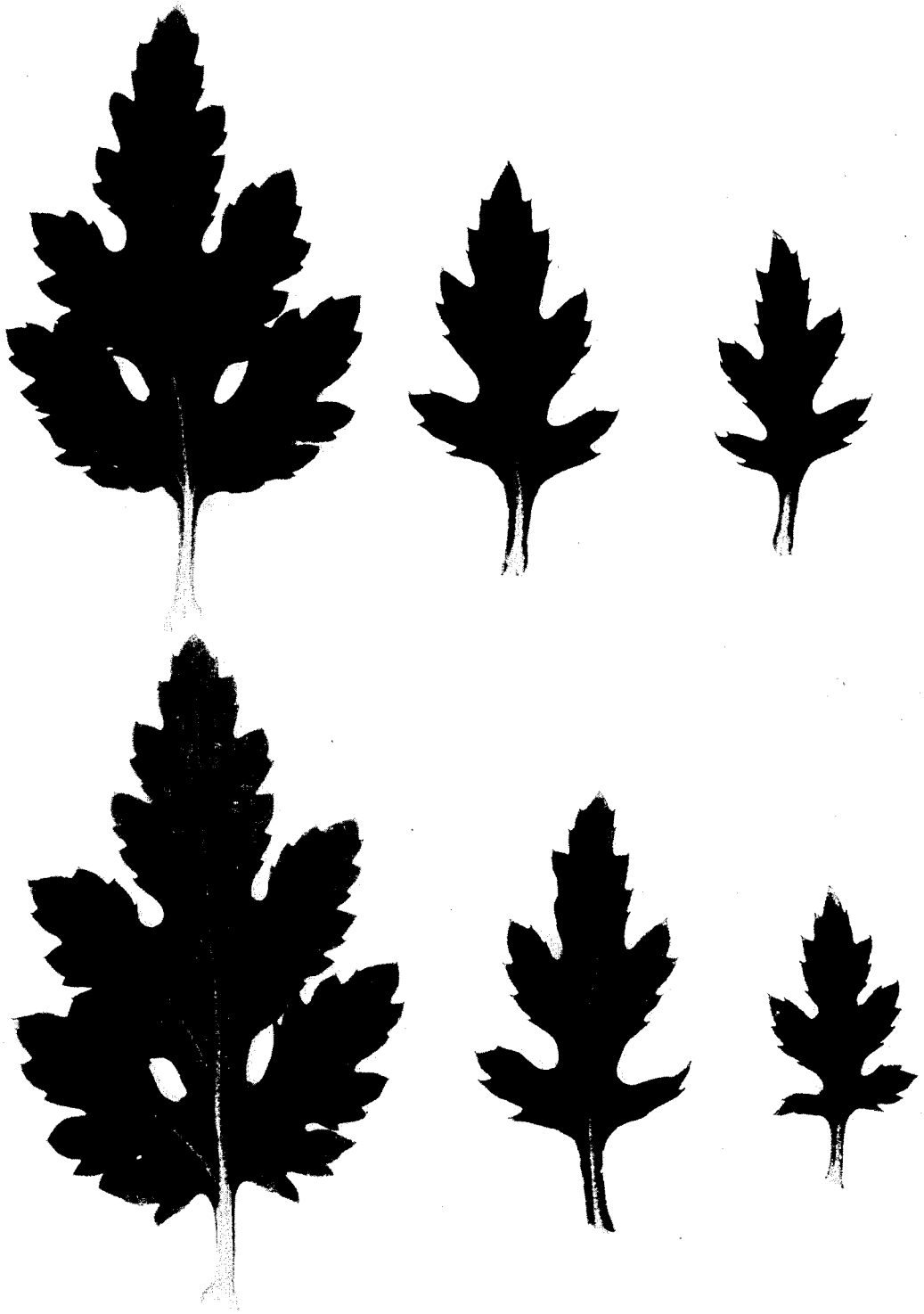

* * * * *